US008563261B2

(12) United States Patent
Chacko

(10) Patent No.: US 8,563,261 B2
(45) Date of Patent: Oct. 22, 2013

(54) METHOD OF DIAGNOSING AND TREATING INTERSTITIAL CYSTITIS

(75) Inventor: Samuel K. Chacko, Media, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 13/498,411

(22) PCT Filed: Sep. 23, 2010

(86) PCT No.: PCT/US2010/049914
§ 371 (c)(1),
(2), (4) Date: Mar. 27, 2012

(87) PCT Pub. No.: WO2011/038063
PCT Pub. Date: Mar. 31, 2011

(65) Prior Publication Data
US 2012/0177665 A1    Jul. 12, 2012

Related U.S. Application Data

(60) Provisional application No. 61/246,273, filed on Sep. 28, 2009.

(51) Int. Cl.
*G01N 33/48* (2006.01)
*G01N 33/53* (2006.01)

(52) U.S. Cl.
USPC .......................................... 435/7.92; 435/7.1

(58) Field of Classification Search
None
See application file for complete search history.

(56) References Cited

U.S. PATENT DOCUMENTS

2003/0143544 A1    7/2003    McCarthy

FOREIGN PATENT DOCUMENTS

WO    WO02/069906        9/2002
WO    WO02/069906    *   9/2012

OTHER PUBLICATIONS

Luscher et al., (Circulation, 2000;102:2434-2440).*
Wilbert-Lampen et al., (Circulation. 1998; 98:385-390).*
Duan et al (Yonsei Medical Journal, 1999; vol. 40, No. 5, pp. 425-429).*
Mayeux et al. ("Biomarkers: Potential uses and Limitations"; NeuroRx (2004); vol. 1, pp. 182-188).*
Latifpour et al., (Journal of Urology 2004; vol. 172., pp. 1235-1236).*
Butrick et al., JSLS (2007)11:182-189 p. 184 first full paragraph , left.*
Oliai et al., 2004; retrieved from URL: www.propath.com/images/pdf_files/Uro/oliai%20series%202%20v5_v09081_lowres.pdf).*
Chen et al., (Sichuan Da Xue Xue Bao Yi Xue Ban, May 2009; 40(3):422-5).*
Ando et al., (Nephron, 1991;57:36-39).*
Bajory er al.,(The journal of urology, 2002;vol. 168, 1222-1225).*
Calvert et al., Clinical Science (2002) 103 (Suppl. 48), 459S-463S.*
Commercial ELISA May 2009; retrieved from URL:www.tecomedical.com/downloads/pdf/The%20Cardiovascular%20Product%20Line.pdf ).*
Bajory Z et al, "The Role of Endothelin-1 in Ischemia-Reperfusion induced Acute Inflammation of the Bladder in Rats", *J. Urology*, Sep. 2002, 168(3):1222-5.
Battistini B, et al., "Growth regulatory properties of endothelins" *Peptides*, Mar. 1993; 14(2): 385-99.
Birder LA, et al, "Feline interstitial cystitis results in mechanical hypersensitivity and altered ATP release from bladder urothelium." *Am J Physiol Renal Physiol* Sep. 2003;285(3):F423-F429.
Carducci MA, et al. "Atrasentan, an endothelin-receptor antagonist for refractory adenocarcinomas: safety and pharmacokinetics." *J Clin Oncol* Apr. 15, 2002;20(8):2171-80.
D'Amico M, et al. "Endothelin-1 in periaqueductal gray area of mice induces analgesia via glutamatergic receptors." *Pain*, May 1996; 65(2-3): 205-9.
Davenport AP, "Analysis of endothelins by enzyme-linked immunosorbent assay and radioimmunoassay." *Methods Mol Biol*, 2002; 206:21-36.
Dell Jr. "Chronic pelvic pain of bladder origin: a focus on interstitial cystitis." *Int J Fertif Womens Med*, Jul. 2003; 48(4): 154-62.
Dosanjh A, et al., "Endothelin-1 (Et-1) decreases human bronchial epithelial cell migration and proliferation: implications for airway remodeling in asthma," *J Asthma*, Dec. 2003; 40(8):883-6.
Erickson Dr, "Urine markers of interstitial cystitis." *Urology* Jun. 2001; 57(6 Suppl 1): 15-21.
Erickson D., et al. "Urine markers do not predict biopsy findings or presence of bladder ulcers in interstitial cystitis/painful bladder syndrome." *J Urology* May 2008;179(5):1850-6. Epub Mar. 18, 2008.
Ferreira SH, et al, "Endothelin-1 participation in overt and inflammatory pain," *J Cardiovasc Pharmacol*, 1989; 13(suppl 5): S220-S222.
Fisher SA, et al, "Endothelin-1 alters the contractile phenotype of cultured embryonic smooth muscle cells." *Circ Res* Jun. 1997;80(6):885-93.
Gamper M. et al., "Gene expression profile of bladder tissue of patients with ulcerative interstitial cystitis", Apr. 2009, *BMC Genomics*, 10:199.

(Continued)

*Primary Examiner* — Jacob Cheu
*Assistant Examiner* — Carmencita M Belei
(74) *Attorney, Agent, or Firm* — Howson & Howson LLP

(57) ABSTRACT

A method for diagnosing, or differentially diagnosing, interstitial cystitis (IC) involves detecting or measuring increased expression of a biomarker Endothelin 1 (ET-1) in a biological sample from a mammalian subject, particularly in the urine or urothelial tissue. An increased level of expression of ET-1 above the level of expression in the same sample of a healthy mammalian subject is an indication of a diagnosis of IC. Such diagnosis may further involve identify other clinical symptoms of IC. Additionally the method may use additional biomarkers, such as Hb-EFG, EGF, APF, IL-8, IL-6, and cGMP. Assay methods and diagnostic reagents and kits for such diagnosis are provided. Methods and compositions for treating IC by reducing the action, production or synthesis of ET-1 in the urine or urothelium and/or inhibiting its binding to its $ET_A$ and/or $ET_B$ receptors are also provided.

5 Claims, 3 Drawing Sheets

(56) References Cited

OTHER PUBLICATIONS

Hanno P. "Painful bladder syndromes." *Clinical Manual of Urology*, 2001, 199-2120.

Jones CA, "Epidemiology of interstitial Cystitis", *Urology*, May 1997; 49(5A Supp ):2-9.

Kaski JC, et al."Concentration of circulating plasma endothelin in patients with angina and normal coronary angiograms." *Br Heart J* Dec. 1955;74(6):620-4.

Keay S, et al, "Decreased 3H0thymidine incorporation by human bladder epithelial cells following exposure to urine from interstitial cystitis patients." *J Urol*, Dec. 1996: 156(6):2073-8.

Keay S, et al. "Antiproliferative factor, heparin-binding epidermal growth factor like growth factor, and epidermal growth factor: sensitive and specific urine markers for interstitial cystitis." *Urology*, Jun. 2001: 57 (6 Suppl 1): 104.

Keay S, et al. "An antiproliferative factor from interstitial cystitis patients is a frizzled 8 protein-related sialoglycopeptide." *Proc Natl Acad Sci USA*, Aug. 2004; 101(32):11803-8.

Khodorova A, et al. "Local injection of a selective endothelin-B receptor agonist inhibits endothelin-1-induced pain-like behavior and excitation of nociceptors in a naloxone-sensitive manner." *J Neurosci* Sep. 1, 2002;22(17):7788-96.

Kim J, et al. "p53 mediates interstitial cystitis antiproliferative factor (APF)-induced growth inhibition of human urothelial cells." *FEBS Lett* Aug. 7, 2007;581(20):3795-9.

Latifpour J. "Endothelins and Bladder Neural Mechanisms", *J. Urol.*, Oct. 2004; 172(4 Pt 1); 12365-6.

Lotz M, et al., "Interleukin-6 and interstitial cystitis." *J Urol.*, Sep. 1994;152(3):869-73.

McGregor E, et al., "Circumferential stretching of saphenous vein smooth muscle enhances vasoconstrictor responses by Rho kinase-dependent pathways." *Cardiovasc Res* Jan. 2002; 53(1):219-26.

Ogawa T, et al., Therapeutic Effects of Endothelin—A Receptor Antagonist on Bladder Overactivity in Rats with Chronic Spinal Cord Injury, Feb. 2008, *J. Urology*, 71:341-345.

Ohta K, et al., "Cytokine-induced release of endothelin-1 from porcine renal epithelial cell line" *Biochem Biophys Res Commun.*, Jun. 15, 1990;169(2):578-84.

Pantettieri RA, Jr., et al. "Endothelin-l-induced potentiation of human airway smooth muscle proliferation: an ETA receptor-mediated phenomenon." *Br J Pharmaco* May 1996; 118(1): 191-7.

Parsons CL. "The therapeutic role of sulfated polysaccharides in the urinary bladder." *Urol Clin North Am.*, Feb. 1994; 21(1):93-100.

Parsons CL, et al., "The role of urinary potassium in the pathogenesis and diagnosis of interstitial cystitis" *J Urol.*, Jun. 1998; 159(6):1862-6.

Pauwels E, et al., "Normality of bladder filling studied in symptom-free middle-aged women." *J Urol.*, Apr. 2004; 171(4): 1567-70.

Piovezan AP, et al., "Effects of endothelin-1 on capsaicin-induced nociception in mice." *Eur J Pharmacol* Jun. 12, 1998: 351(1):15-22.

Raffa RB, et al, "Endothelin-1-induced nociception" *Life Sci.*, 1991; 49911: L61-L65.

Shea VK, et al, "Sensory fibers of the pelvic nerve innervating the Rat's urinary bladder." *J. Neurophysiol* Oct. 2000; 84(4):1924-33.

Shirasawa Y, et al., "Stretch-induced calcium sensitization of rat lymphatic smooth muscle." *Am J Physiol Heart Circ Physiol* Dec. 2003;285(6):H2573-77.

Shokeir AA, "Role of Urinary Biomarkers in the Diagnosis of Congenital Upper Urinary Tract Obstruction", *African J. Urol.*, 2007, 13(3):179-187.

Steinkohl WB et al., "Urodynamic findings in interstitial cystitis." *Urology*, Dec. 1989;34(6):399-401.

Su X, et al, "Effects of opioids on mechanosensitive pelvic nerve afferent fibers innervating the urinary bladder of the bat." *J Neurophysiol* Mar. 1997;77(3): 1566-80.

Sumpio BE, et al, "Enhanced production of endothelium-derived contracting factor by endothelial cells subjected to pulsatile stretch." *Surgery*, Aug. 1990; 108(2): 277-81.

Sun Y, et al, "Augmented stretch activated adenosine triphosphate release from bladder uroepithelial cells in patients with interstitial cystitis." *J Urol*, Nov. 2001;166(5):1951-6.

Tomaszewski JE, et al., "Biopsy features are associated with primary symptoms in interstitial cystitis: results from the interstitial cystitis database study." *Urology*. Jun. 2001: 57(6 Suppl 1):67-81.

Uehata M, et al., "Calcium sensitization of smooth muscle mediated by a Rho-associated protein kinase in hypertension." *Nature*. Oct. 30, 1997;389(6654);990-4.

Yanagisawa M, et al, "A novel potent vasoconstrictor peptide produced by vascular endothelial cells" *Nature*. Mar. 31, 1988; 332(6163):411-5.

Zamore PD, et al., "Ribo-gnome: the big world of small RNAs." *Science*. Sep. 2005; 309(5740):1519-24.

Zhang EY, et al., "Smooth muscle hypertrophy following partial bladder outlet obstruction is associated with overexpression of non-muscle caldesmon." *Am J Pathol* Feb. 2004;164(2):601-12.

Human Endothelin-1 Enzyme Immunometric Assay Kit, Catalog No. 900-020, Assay Designs, Copyright 1997.

Transmittal of the International Search report and Written Opinion of corresponding PCT/US2010/049914, dated Mar. 17, 2011.

International Preliminary Report on Patentability of corresponding PCT/US2010/049914, dated Apr. 3, 2012.

* cited by examiner

METHOD OF DIAGNOSING AND TREATING INTERSTITIAL CYSTITIS

CROSS-REFERENCE TO RELATED APPLICATIONS

This application is a national stage of International Patent Application No. PCT/US2010/049914, filed Sep. 23, 2010, which claims the benefit of the priority of U.S. Provisional Patent Application No. 61/246,273, filed Sep. 28, 2009 (expired), which applications are incorporated herein by reference.

BACKGROUND OF THE INVENTION

Interstitial cystitis, also known as painful bladder syndrome, is a pathological condition that affects as many as 1 million patients in the U.S. with a high incidence in females. A heterogeneous array of symptoms varies from case to case and even in the same individual. Such symptoms can include mild discomfort, pressure, tenderness, intense pain in the bladder and pelvic area, increased urinary frequency/urgency, nocturia or a combination of these symptoms[12]. Pain may change in intensity as the bladder fills with urine or as it empties. People with interstitial cystitis also have a defect in the protective lining (transitional epithelium; also urothelium) of the bladder. The loss of the integrity of the urothelium is suspected to lead to leaky epithelium lining the bladder wall and allow toxic substances in urine to irritate the bladder wall.

The etiology of IC is complex including inflammation, infection, hormone involvement, autoimmunity, psychological effects, and genetic implications. The pathogenesis of IC involves inflammation, neural changes, urothelial dysfunctions, hypersensitivity, fibrosis, oxidative stress and apoptosis in the development and progression of this painful bladder syndrome. Tomazewski et al.[2] investigated the association between the pathologic changes in the bladder biopsies with urinary bladder dysfunction among 204 IC patients enrolled in the Interstitial Cystitis Database (ICDB). The pathologic changes noted were increased number of mast cells in the lamina propria, loss of urothelium, granulation tissue and increased vascular density in the lamina propria, and submucosal hemorrhage. Thus, the lesion in the bladder appears to center in the epithelium and the lamina propria of the bladder.

Patients with IC have substantially lower cystometric bladder volumes compared to normal women (265 ml versus 586 ml) and first voiding desire is at 74 ml compared to 315 ml for normal[3,4]. This suggests that the mechanoreceptors and chemoreceptors in the bladder of IC patients may be altered, and this may trigger myelinated A-δ fibers or C-fibers found in the detrusor smooth muscle or the submucosa in response to bladder distention[5,6]. Although there are several hypotheses to account for the pathogenesis of IC, a widely accepted theory focuses on urothelial dysfunction. The urothelium, covered by proteoglycan and uroplakin, prevents the adhesion of infectious organisms, and the entrance of irritating urinary solutes into the interstitium[7]. A glycosylated frizzled-related peptide (APF) which inhibits the proliferation of urothelial cell is secreted by urothelial cells from patients with IC[8]. A defective urothelium is less protective, allowing urinary solutes like potassium to leak into the mucosa and submucosal region[9]. This can lead to activation of C-fibers, release of substance P and mast cell degranulation and subsequent injury to the submucosal tissue. These tissue changes lead to neuronal activation, leading to urinary urgency/frequency and pelvic pain associated with IC[10].

Current diagnostic tests for IC include urinalysis for evidence of a urinary tract infection, urine culture and cytology, and potassium sensitivity tests. Still other diagnostic tests include cystoscopy, i.e., an examination of the bladder through a cystoscope inserted through the urethra. Additionally, cystodistension performed with anesthetics can determine the bladder's capacity. In males, a diagnostic procedure can include laboratory examination of prostate secretions.

It is difficult to make a clear diagnosis of IC because clinicians are hampered by the lack of biomarkers to either evaluate the symptoms, pathological changes, and pathogenesis of the condition and/or to provide appropriate treatments. Even when a mode of treatment is selected and tried, it is difficult to evaluate the effect of treatment for inducing beneficial changes in the bladder wall, the urothelium and the suburothelial regions, which are severely affected in IC. Most biomarkers for IC or related syndromes that were analyzed in the past were inflammatory cytokines (such as IL-Iβ, IL-6, TNFα). Significant levels of IL-6 were found in the urine and bladder wall of patients in one study[14]. Another study[34, 35] suggested the difficulty of correlating urine biomarkers such as IL-6 and IL-8 and biopsy findings, although a strong association between urine IL-8 and bladder mast cell count was found.

The presence of an anti-proliferative factor (APF), a low molecular weight sialoglycopeptide, and potent inhibitor of the growth of normal urothelial cells and bladder cancer cells[8] was documented in the urine of patients with IC. The specificity of APF in urine from patients with IC (versus normal controls and patients with a variety of other urogenital disorders) indicates that it may be a useful biomarker for IC. A recent publication[41] referred to gene expression profiles of bladder tissues of patients with ulcerative IC. This study used very little urothelium because the urothelial layer was denuded due to ulceration.

There remains a need in the art for simpler, less invasive and more accurate diagnostic assays for IC, as well as for new and more effective treatments of this disorder.

SUMMARY OF THE INVENTION

In one aspect, a method is provided for diagnosing interstitial cystitis (IC), or differentially diagnosing IC from other infections or inflammatory conditions of the bladder or urinary tract. The method includes measuring the level of expression of a biomarker Endothelin 1 (ET-1) in a biological sample from a mammalian subject, preferably a human subject. When compared to the level of expression of ET-1 in a healthy mammalian subject, an increased level of expression is an indication of a diagnosis of IC. More particularly, this method is demonstrated when the biological sample is urine or urothelial cells or urothelial tissue.

In another aspect, a diagnostic method for IC involves measuring the level of expression of ET-1 and at least one additional biomarker in the above-noted biological sample. The combined changes in expression of ET-1 and the additional biomarker from their respective levels of expression in a healthy mammalian subject is an indication or differential indication of a diagnosis of IC. Further differential diagnoses may be performed by combining the biomarker measurements with other clinical symptoms of IC.

In another aspect, a method is provided for monitoring progression of IC in a mammalian subject suffering from that disorder. In this method the level of expression of ET-1 in a biological sample from a mammalian subject having IC is measured and compared to the level of expression of ET-1 of a temporally earlier biological sample of the same subject. In this method, a decreased expression level of the ET-1, particularly in the urine or urethelium of the subject, compared to that in an earlier biological sample of the same subject is indicative of regression or improvement in the disorder. Conversely, an increase in ET-1 in the later sample is indicative of progression or increase in severity of the disorder. As one embodiment, this method can be applied to a subject being treated for IC. In this circumstance, the method enables a determination of the efficacy of the treatment.

In other aspects of the methods described herein, the methods may include a variety of known assay formats capable of identifying the presence of ET-1. In certain embodiments, such a method may employ use of certain machines or computer-programmed instruments that can transform detectable signals generated from diagnostic reagents complexed with the ET-1 present in the biological sample into numerical or graphical data useful in performing the diagnosis. In one embodiment, the diagnosis or differential diagnosis based on the identification or measurement of the ET-1 level in a subject's sample is associated with the presentation of certain clinical symptoms in a subject. In another embodiment, the diagnosis provides a quantitative assessment of the likelihood of IC occurrence in a subject that has not yet developed clinical symptoms of IC.

In another aspect, a diagnostic composition or kit for diagnosing or differentially diagnosing the occurrence, stage or progression of IC in a mammalian subject is provided. In one aspect, the composition contains one or a plurality of polynucleotides immobilized on a substrate, wherein at least one polynucleotide is a genomic probe that hybridizes to ET-1 mRNA. In another aspect, the composition contains one or a plurality of PCR primer-probe sets, wherein at least one primer-probe set amplifies a polynucleotide (mRNA) sequence of ET-1. In another aspect, the composition contains one or a plurality of ligands, such as antibodies or fragments, wherein at least one ligand binds to ET-1 in a biological sample of a mammalian subject. In other embodiments, the other polynucleotides or other primer-probe sets or other ligands are designed to detect additional biomarkers. Such diagnostic compositions may also contain conventional labels which emit detectable signals when complexes with the ET-1 in the sample are formed.

In another aspect, a method for treating interstitial cystitis includes delivering to a mammalian subject in need thereof a therapeutic composition that inhibits the action of ET-1 or reduces the amount or production of ET-1, particularly in the bladder. In another aspect, a method for treating interstitial cystitis includes delivering to a mammalian subject in need thereof a therapeutic composition that inhibits the action or expression of ET-1 in the urothelial cells of the subject. In another aspect, a method for treating interstitial cystitis includes delivering to a mammalian subject in need thereof a therapeutic composition that inhibits the binding of ET-1 with its receptors ($ET_A$ and $ET_C$) on urothelial cells. In still another aspect, a method for inhibiting urothelial cell proliferation includes delivering to a mammalian subject in need thereof an effective amount of a reagent that inhibits ET-1 production, synthesis or action in the bladder, e.g., an ET-1 antagonist, $ET_A$ or $ET_B$ receptor antagonist or a functional fragment thereof.

In yet another aspect, there is provided a use of ET-1 or a ligand for ET-1 or primer or probe capable of hybridizing to ET-1, or other biomarker noted below, in the diagnosis or assessment of differential diagnosis, or for monitoring the progression of IC in a subject.

In yet another aspect, there is provided a use of a composition that inhibits the action of ET-1 or the binding of ET-1 with its receptors, or reduces the amount or production of ET-1, in a method for treating interstitial cystitis.

Other aspects and advantages of the invention are described further in the following detailed description of the preferred embodiments thereof.

DETAILED DESCRIPTION OF THE INVENTION

Figure 1:
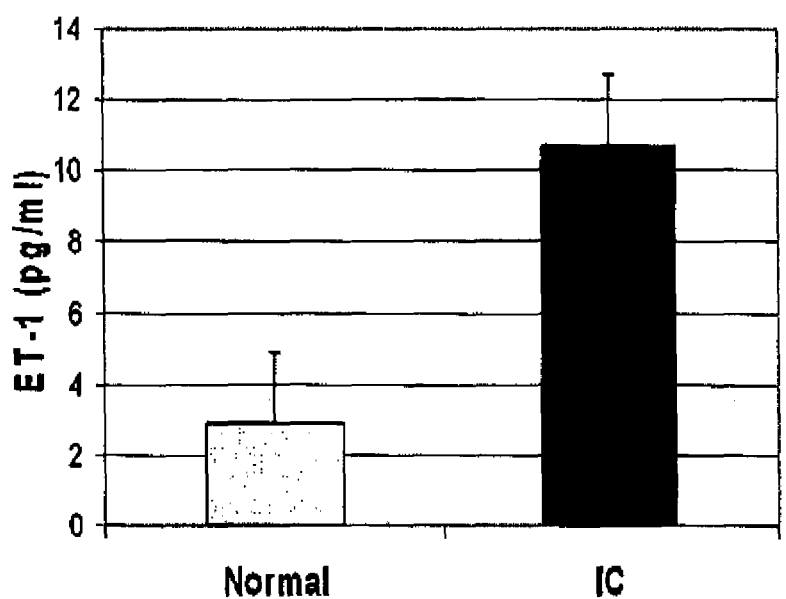
FIG. 1 is a bar graph showing the results of an ELISA assay for ET-1 in human urine. The concentration of ET-1 in the urine of female patients with IC (n=5; dark bar) is contrasted with that of normal healthy women (n=4; light bar). The results show that the average ET-1 level is 2.9±1.9 pg/ml in urine from the normal control group. The average ET-1 level increases to 10.7±2.3 pg/ml in urine from IC patients. These data from five women with IC compared with that from four normal women, indicates that there is an increased amount of Endothelin in the urine of patients with IC.

In response to the need in the art, methods for diagnosing and/or monitoring the progress, or response to therapeutic regimen, of interstitial cystitis (IC) in a mammalian subject involve employing endothelin-1 (ET-1) as a biomarker. The invention provides a previously unrecognized correlation between urine/urothelial cell ET-1 levels in mammalian subjects and the occurrence or progression of interstitial cystitis. Compositions for performing such diagnostic methods and therapeutic methods for treating IC are also disclosed.

As evidenced in the examples below and summarized here, the inventors found that in patients clinically diagnosed with IC vs. normal controls, a correlation exists between elevations of ET-1 and IC that has not been shown before. Thus, ET-1, and particularly its level in the urine or expression level in urothelial cells of a subject suspected of having IC, serves as a biomarker for IC. It is also found that ET-1 lowers the proliferation of urothelial cells and the ET-1-induced inhibition of urothelial proliferation is reversed by a global ET-1 antagonist. It is further theorized that the high level of ET-1 in the urine and the urothelial cells prevents the proliferation and repair of urothelial lining, which loses urothelial integrity. Passage of the toxic solutes from the urine into the urothelium increases irritation and aggravation of the inflammatory process in IC.

A. Diagnostic/Prognostic Methods for Interstitial Cystitis

Novel methods for performing a diagnosis of interstitial cystitis (IC) in a mammalian subject or a differential diagnosis of IC versus other infections or inflammatory conditions of the bladder or urinary tract involves evaluating levels of endothelin-1 (ET-1) in a biological sample of a mammalian subject.

By the phrase "biological sample" is meant urine, urine containing shed urothelial cells or sedimented urothelial cells, or tissue biopsies from the urothelium. In certain embodiments, a sample may be another fluid or tissue containing urothelial cells, either benign or malignant cells. While the methods described herein may be operative in other biological samples, such as whole blood, serum or plasma, saliva, semen, and cellular exudates from a mammalian subject, as well as tissue biopsies, it is more relevant to the loss of integrity of the urothelium to detect the biomarker in fluids or cells from the bladder cavity. Such samples may further be diluted with saline, buffer or a physiologically acceptable diluent. Alternatively, such samples are concentrated by conventional means.

By the terms "patient" or "subject" as used herein means a mammalian animal, including a human, a veterinary or farm animal, a domestic animal or pet, and animals normally used for clinical research. More specifically, the subject of these methods and compositions is a human. In one aspect of the methods described herein, the subject undergoing the diagnostic or therapeutic method is asymptomatic for IC. In another aspect, the subject undergoing the diagnostic or therapeutic methods described herein shows clinical signs of IC.

As used herein, the term "reference standard" refers to in one embodiment, one or more identical samples from the same subject, but collected at a different time, or in another embodiment, one or more samples from one or more different subjects who are healthy; or in another embodiment, to one or more samples from one or more different subjects who have IC or another related disorder. In still another embodiment, the reference standard is a numerical average or average range of the expression of a biomarker in a defined population, rather than a single subject. For example, in one embodiment, a reference standard for a biomarker in a healthy subject is a numerical value or range for expression of that biomarker in a population of average healthy subjects. Likewise, in an alternative embodiment, a reference standard for the expression of a biomarker in a subject with a disease at a certain stage of severity is a numerical value or range for the average expression of that biomarker in a population composed of multiple patients with the disease at a certain stage of severity.

The biomarker, Endothelin-1 (ET-1), is a potent vasoconstrictor peptide with 21 amino acid residues[31]. The nucleotide and amino acid sequences of ET-1 for humans and other mammals are known. See, e.g., GenBank database Accession Nos. NM_001955 and AAA52339 for the human nucleotide and amino acid sequences of the pre-protein and mature "big" and "small" forms of ET-1. Such sequences may also include known variants or mutations of ET-1. By "ET-1" as used herein is meant the small form of the mature protein, characterized in humans by the 21 amino acid sequence CSCSS-LMDKECVYFCHLDIIW (SEQ ID NO: 1) or a functional fragment thereof. By the term "functional fragment" is meant any fragment of a nucleotide or amino acid sequence that shares the same biological function of the entire sequence.

Figure 2A:
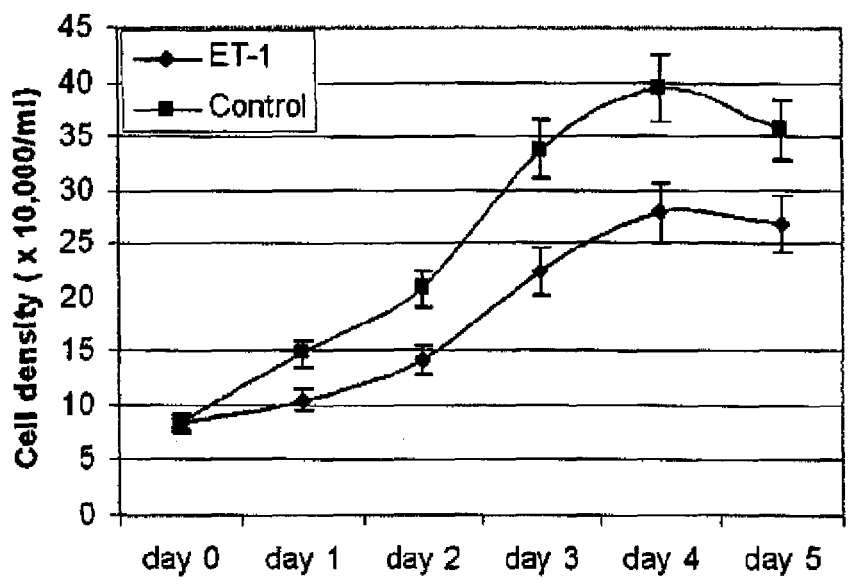
FIG. 2A is a graph showing the effect of ET-1 on growth of cultured rabbit primary urothelial cells. The graph shows a 30-40% inhibition of growth of rabbit primary urothelial cells by ET-1 at 20 μM.
Figure 2B:
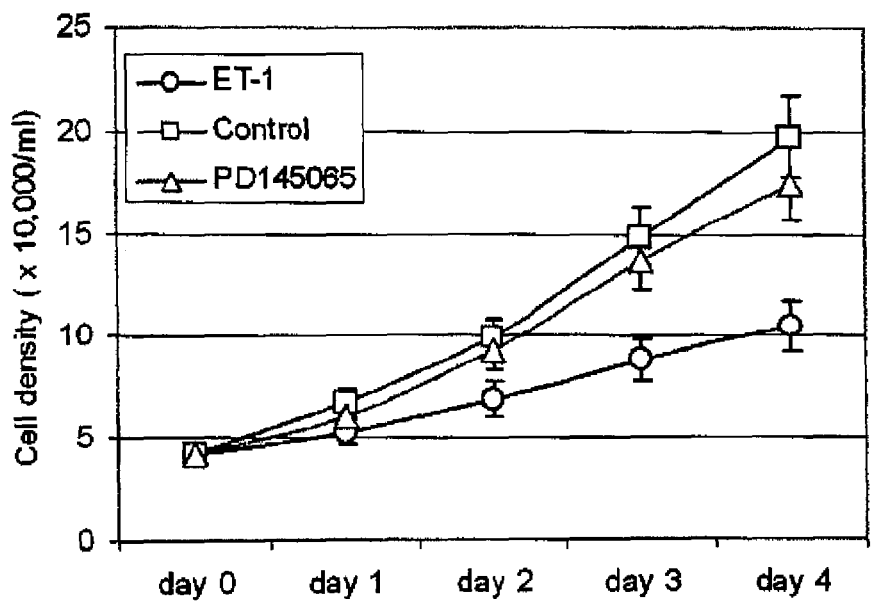
FIG. 2B is a graph showing the effect of ET-1 on growth of cultured human primary urothelial cells. This graph shows the inhibition of 20 μM ET-1 on the cell growth of cultured human urothelial cells and this inhibition is reversed by 1 μM PD145065 (Sigma Chemicals, St. Louis, Mo.; a global ET-1 receptor antagonist that inhibits both $ET_A$ and $ET_B$). The fact that the ET-1 receptor antagonist abolishes the ET-1-induced anti-proliferative effect show that ET-1's effect is receptor-mediated.
Figure 3:
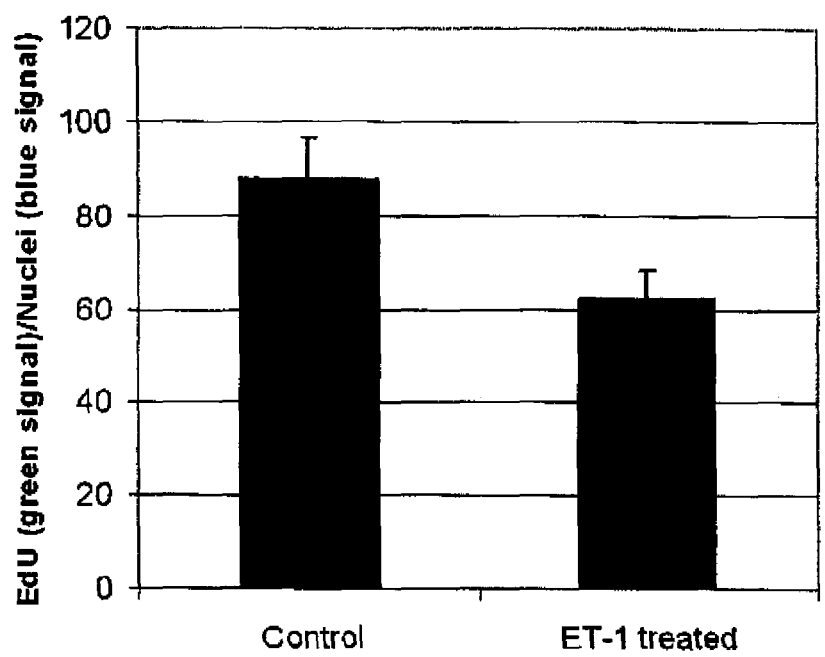
FIG. 3 is a bar graph showing and quantifying newly synthesized DNA by detecting EdU, a nucleoside analog of thymidine that is incorporated in DNA during active DNA synthesis for both control urothelial cells and ET-1-treated urothelial cells. ET-1 treatment (10 nM, which is equal to 25 ng/ml) induced a significant decrease of EdU staining in cultured urothelial cells, which means less newly synthesized DNA in the presence of ET-1.

The receptors for endothelin, $ET_A$ and $ET_B$, originally found in the endothelium of blood vessels have been found in many other organs. ET-1 promotes the growth of various cell types, such as fibroblasts, mesangial cells, and endothelial cells[32]. On the other hand, ET-1 decreases human bronchial epithelial cell migration and proliferation[33]. ET-1 has been shown to act as a potent growth factor for smooth muscle[20] and it has also been shown to have an effect on the contractile phenotype of smooth muscle as well[21]. In contrast to the mitogenic effect that ET-1 has on smooth muscle cells, it has been shown to have an antiproliferative effect on cultured urothelial cells (as shown in FIGS. 2A, 2B and 3). ET-1 is released upon stretch[22-24]. In addition, ET-1 release is stimulated by cytokines[25,26]. ET-1 is also a mediator of pain. Increased levels of ET-1 have been associated with labor pain and angina[14]. In addition, abdominal constriction induced by ET-1 in rats was shown to be blocked by morphine. Surprisingly, ET-1 has also been associated with analgesia[19]. It has been suggested that the two main endothelin receptor subtypes may determine the specific effect produced with activation of $ET^A$ receptors triggering pain[21] and activation of $ET^B$ receptors producing analgesia[19,20].

Unless defined otherwise in this specification, technical and scientific terms used herein have the same meaning as commonly understood by one of ordinary skill in the art to which this invention belongs and by reference to published texts.

In one aspect, a method for diagnosing, or differentially diagnosing, interstitial cystitis (IC) thus includes measuring the level of expression of ET-1 in a biological sample from a mammalian subject. In one embodiment, such a method involves contacting a sample with a diagnostic reagent capable of forming a complex or association with the ET-1 in the sample; followed by detecting or measuring the level of the complex or association thus formed. Upon comparison with ET-1 levels in a biological sample healthy mammalian subject (or a reference standard developed from an average of ET-1 levels in a normal healthy mammalian population), an increased level of expression of ET-1 is an indication of a diagnosis of IC. In one aspect, the increased expression of ET-1 in the urine or a sample containing urothelial cells of a subject having at least one clinical symptom of IC provides a diagnosis of the disease. Thus, ET-1 is a newly found biomarker for IC. In another embodiment, ET-1 is employed in a differential diagnosis with other biomarkers or with the assessment of other clinical symptoms indicative of IC.

While such comparison can occur by direct comparison of the ET-1 measurement in the subject's biological sample with the expression levels in similar samples of one or more healthy subjects, it is more typical for a reference average expression level to be provided as a number or range. A level of expression of ET-1 in the subject's sample that is above the level of expression in a healthy mammalian subject (or reference average) is an indication of a diagnosis or a differential diagnostic indicator of IC.

Similarly, a method for monitoring progression of IC in a mammalian subject involves measuring the level of expression of ET-1 in a biological sample from a mammalian subject having IC over a given time period. In one embodiment, such a method involves contacting a sample with a diagnostic reagent capable of forming a complex or association with the ET-1 in the sample; followed by detecting or measuring the level of the complex or association thus formed. The expression level of ET-1 is then compared with the level of expression in one or more biological samples of the same subject assayed earlier in time, or before or during treatment. While such comparison can occur by direct comparison with one or more prior assessments of the same patient's status, it is also possible for a reference average expression level at specific stages or severities of the disease among other patients with IC to be provided as a reference number or profile. A decreased expression level of the ET-1 in the urine or urethelium of the subject compared to that of an earlier biological sample of the same subject or reference average is indicative of regression of said IC. A level of expression of the ET-1 in the subject's sample that is above the subject's prior level of expression (or reference average) is an indication of a poor prognosis or increasing severity of the disease. In circumstances under which the subject is being treated for IC, this method is useful to determine the degree of success or efficacy of a particular therapeutic regimen for IC. This method may indicate circumstances in which a change of therapy is necessary.

By the phrase "above the level of expression" is meant to refer to concentration of ET-1 when the protein's concentration generally in urine or another body fluid is measured. However, this phrase can also refer to relative increases in expression observed in subject's tissue from normal tissue by immunohistochemical (IHC) staining (see Example 2) as well as by calculating the numerical concentration from the IHC results. Any method by which one of skill in the art may detect an increase or change in expression of the biomarker is encompassed by that phrase and by the methods described herein.

The measurement of ET-1 concentration, preferably in urine or urothelial biopsy tissue, serves as a biomarker for IC. According to the method of this invention, to determine a diagnosis or to assess progression or response to treatment of IC, the level of ET-1 protein in a biological fluid of a mammalian subject is measured and compared to a reference standard of ET-1 levels in a normal healthy mammalian population. In one embodiment, such a method involves contacting a sample with a diagnostic reagent capable of forming a complex or association with the ET-1 in the sample; followed by detecting or measuring the level of the complex or association thus formed. An elevated ET-1 level in the subject's biological sample compared to that standard can diagnose or aid in confirming diagnosis of IC obtained by other methods, e.g., clinical symptoms.

One suitable reference standard is that established by measuring ET-1 values of a normal population sample. Thus, the standard is preferably provided by using the same assay technique as is used for measurement of the subject's ET-1 levels, to avoid any error in standardization. As demonstrated in the examples below, the relative level of risk of IC can be determined based upon the increase of ET-1 as compared against the ET-1 levels of a population. As demonstrated by the examples below, the occurrence of IC is associated with increased levels of ET-1 in urine and increased expression of ET-1 in urothelial tissue.

As described above, "normal" levels of ET-1 in a population can vary based upon any variables in an individual assay used for measurement and the standardization of regents employed in such assay. Therefore, in one embodiment of this invention, i.e., that based upon the assay and antibody employed in the examples below, the "normal" level of urinary ET-1 ranges between and including the concentrations 1.0 and 4.0 pg/ml. For example, according to the ELISA assay employed in the examples below, average levels of urinary ET-1 were 2.9±1.9 pg/ml in urine from the normal control group. However, in another assay, the "normal" value may skew somewhat from the minimum average of 1.0 pg/ml or maximum average of 4.0 pg/ml. Increasingly sensitive assays may further affect the "normal" range of ET-1 in the biological samples of a population. However, other averages within the ranges may be obtained for larger populations or populations of patients differing in other physiological characteristics, e.g., gender, weight, physical condition, etc. or for other types of biological samples.

Thus, for purposes of this invention when using an ELISA, particularly the ELISA and reagents of the examples below, a diagnosis of IC may be obtained when a subject's urinary ET-1 is significantly elevated above 4.0 pg/ml. For example, the results of Example 3 demonstrate that the average urinary ET-1 concentration in IC patients was 10.7±2.3 pg/ml. Thus, in one embodiment of the diagnostic method of this invention a diagnosis of IC may be made when a subject's urinary ET-1 level is greater than 4 pg/ml. In another embodiment of the diagnostic method of this invention a diagnosis of IC may be made when a subject's urinary ET-1 level is greater than 5 pg/ml. In yet another embodiment of the diagnostic method of this invention a diagnosis of IC may be made when a subject's urinary ET-1 level is or greater than 6 pg/ml. In yet another embodiment of the diagnostic method of this invention a diagnosis of IC may be made when a subject's urinary ET-1 level is or greater than 7 or 8 pg/ml. In yet another embodiment of the diagnostic method of this invention a diagnosis of IC may be made when a subject's urinary ET-1 level is or greater than 9 or 10 pg/ml, and so on.

Alternatively, a diagnosis of IC may be obtained when the elevation in ET-1 expression is noted in a sample containing shed or sedimented urothelial cells expressing ET-1. Still alternatively, a diagnosis of IC may be obtained when the elevation in ET-1 expression is noted by a relative increase in expression of ET-1 in biopsy tissue samples, particularly urothelial cells of the bladder or urinary tract when contrasted with "normal" cells or tissues. See, e.g., Example 2 which demonstrates an increase in urothelial ET-1 observed by immunohistochemical microscopy.

In still a further embodiment of methods according to this invention, a differential diagnosis of IC in a subject may be performed by measuring ET-1 levels in combination with measuring one of more second or other IC biomarkers and/or coupled with clinical symptoms of IC. In one aspect, the diagnostic or disease monitoring methods described herein further include coupling the measurement of the biomarker ET-1 with measuring the level of expression of at least one additional biomarker in a patient's sample. The combined changes in expression of ET-1 and the additional biomarker from their respective levels of expression in a healthy mammalian subject is an indication of a diagnosis or differential diagnosis, of IC. Among such additional biomarkers diagnostic or useful in a differential diagnosis of IC are urinary or urothelial-related markers, such as Hb-EFG, EGF, APF, IGF-1, IGFBP-3[34,35]. Other useful additional biomarkers are mast cell activation-related markers, such as histamine and methylhistamine[34,35]. Still other additional biomarkers are inflammatory markers, such as IL-8, IL-6, IL-1, nitric oxide gas, and cGMP[34,35]. Still other additional biomarkers are innervation-related markers, nerve growth factors and norepinephrin[34,35].

Correlation between the ET-1 level and a level indicative of IC for the second biomarker further confirms the diagnosis or evaluation of the severity of the IC. Thus the measurement of ET-1 may serve to confirm indications of IC provided by assays for other biomarkers. Alternatively the measurement of ET-1 may serve to more accurately diagnose IC than other biomarkers alone. Still alternatively, the clinical symptoms of IC, e.g., mild discomfort, pressure, tenderness, intense pain in the bladder and pelvic area, increased urinary frequency/urgency, nocturia or a combination of these symptoms, when coupled with the ET-1 measurement provides a more accurate diagnosis of the disease.

As stated above, specific diagnostic methodology employed in the measurement of ET-1 in the biological sample includes measuring the ET-1 as ribonucleic acid (mRNA, i.e., measuring the transcription of ET-1) or protein (i.e., measuring translation of the protein) using conventional assay technologies. In one embodiment, the ET-1 expression is measured in the urothelial cells obtained from punch biopsies or from cells in the urine sediment (obtained after centrifugation) at the mRNA and protein levels, respectively by polymerase chain reaction and enzyme-linked immunosorbent assay (ELISA). The specific methodologies that can be employed to perform the diagnostic methods described herein may be readily selected and adapted by one of skill in the art, including the exemplified ELISA assay for ET-1 in a urine sample and immunohistochemical staining of a urothelium sample.

In one embodiment, the ET-1 expression is measured in the urothelial cells obtained from punch 1. Assays for Protein The measurement of the ET-1 protein (or any second biomarker) in the biological sample may employ as a diagnostic reagent any suitable ET-1 ligand, e.g., antibody (or antibody to any second biomarker) to detect the protein. Such antibodies may be presently extant in the art or presently used commercially, such as those available as part of the ASSAY DESIGNS ET-1 assay kit, or may be developed by techniques now common in the field of immunology. As used herein, the term "antibody" refers to an intact immunoglobulin having two light and two heavy chains or any fragments thereof. Thus a single isolated antibody or fragment may be a polyclonal antibody, a high affinity polyclonal antibody, a monoclonal antibody, a synthetic antibody, a recombinant antibody, a chimeric antibody, a humanized antibody, or a human antibody. The term "antibody fragment" refers to less than an intact antibody structure, including, without limitation, an isolated single antibody chain, a single chain Fv construct, a Fab construct, a light chain variable or complementarity determining region (CDR) sequence, etc. A recombinant molecule bearing the binding portion of an anti-ET-1 antibody, e.g., carrying one or more variable chain CDR sequences that bind ET-1, may also be used in a diagnostic assay of this invention. As used herein, the term "antibody" may also refer, where appropriate, to a mixture of different antibodies or antibody fragments that bind to ET-1. Such different antibodies may bind to a different portion of the ET-1 protein than the other antibodies in the mixture. Such differences in antibodies used in the assay may be reflected in the CDR sequences of the variable regions of the antibodies. Such differences may also be generated by the antibody backbone, for example, if the antibody itself is a non-human antibody containing a human CDR sequence, or a chimeric antibody or some other recombinant antibody fragment containing sequences from a non-human source. Antibodies or fragments useful in the method of this invention may be generated synthetically or recombinantly, using conventional techniques or may be isolated and purified from plasma or further manipulated to increase the binding affinity thereof. It should be understood that any antibody, antibody fragment, or mixture thereof that binds ET-1 or a particular sequence of ET-1 as defined above may be employed in the methods of the present invention, regardless of how the antibody or mixture of antibodies was generated.

Similarly, in suitable diagnostic reagents, the antibodies may be tagged or labeled with reagents capable of providing a detectable signal, depending upon the assay format employed. Such labels are capable, alone or in concert with other compositions or compounds, of providing a detectable signal. Where more than one antibody is employed in a diagnostic method, e.g., such as in a sandwich ELISA, the labels are desirably interactive to produce a detectable signal. Most desirably, the label is detectable visually, e.g. colorimetrically. A variety of enzyme systems operate to reveal a colorimetric signal in an assay, e.g., glucose oxidase (which uses glucose as a substrate) releases peroxide as a product that in the presence of peroxidase and a hydrogen donor such as tetramethyl benzidine (TMB) produces an oxidized TMB that is seen as a blue color. Other examples include horseradish peroxidase (HRP) or alkaline phosphatase (AP), and hexokinase in conjunction with glucose-6-phosphate dehydrogenase that reacts with ATP, glucose, and NAD+ to yield, among other products, NADH that is detected as increased absorbance at 340 nm wavelength.

Other label systems that may be utilized in the methods of this invention are detectable by other means, e.g., colored latex microparticles (Bangs Laboratories, Indiana) in which a dye is embedded may be used in place of enzymes to provide a visual signal indicative of the presence of the resulting ET-1-antibody complex in applicable assays. Still other labels include fluorescent compounds, radioactive compounds or elements. Preferably, an anti-ET-1 antibody is associated with, or conjugated to a fluorescent detectable fluorochromes, e.g., fluorescein isothiocyanate (FITC), phycoerythrin (PE), allophycocyanin (APC), coriphosphine-O (CPO) or tandem dyes, PE-cyanin-5 (PC5), and PE-Texas Red (ECD). Commonly used fluorochromes include fluorescein isothiocyanate (FITC), phycoerythrin (PE), allophycocyanin (APC), and also include the tandem dyes, PE-cyanin-5 (PC5), PE-cyanin-7 (PC7), PE-cyanin-5.5, PE-Texas Red (ECD), rhodamine, PerCP, fluorescein isothiocyanate (FITC) and Alexa dyes. Combinations of such labels, such as Texas Red and rhodamine, FITC+PE, FITC+PECy5 and PE+PECy7, among others may be used depending upon assay method.

Detectable labels for attachment to diagnostic reagents useful in diagnostic assays of this invention may be selected from among numerous compositions known and readily available to one skilled in the art of diagnostic assays. The anti-ET-1 antibodies or fragments useful in this invention are not limited by the particular detectable label or label system employed. Thus, selection and/or generation of suitable anti-ET-1 antibodies with optional labels for use in this invention is within the skill of the art, provided with this specification, the documents incorporated herein, and the conventional teachings of immunology.

Similarly the particular assay format used to measure the ET-1 in a biological sample may be selected from among a wide range of immunoassays, such as enzyme-linked immunoassays, such as those described in the examples below, sandwich immunoassays, homogeneous assays, immunohistochemistry formats, or other conventional assay formats. One of skill in the art may readily select from any number of conventional immunoassay formats to perform this invention.

Other reagents for the detection of protein in biological samples, such as peptide mimetics, synthetic chemical compounds capable of detecting ET-1 may be used in other assay formats for the quantitative detection of ET-1 protein in biological samples, such as high pressure liquid chromatography (HPLC), immunohistochemistry, etc.

2. Nucleic Acid Assay Formats

Still other methods useful in performing the diagnostic steps described herein are known and well summarized in, e.g., U.S. Pat. No. 7,081,340. Such methods include methods based on hybridization analysis of polynucleotides, methods based on sequencing of polynucleotides, proteomics-based methods or immunochemistry techniques. The most commonly used methods known in the art for the quantification of mRNA expression in a sample include northern blotting and in situ hybridization; RNAse protection assays; and PCR-based methods, such as reverse transcription polymerase chain reaction (RT-PCR) or qPCR. Alternatively, antibodies may be employed that can recognize specific DNA-protein duplexes. The methods described herein are not limited by the particular techniques selected to perform them. Exemplary commercial products for generation of reagents or performance of assays include TRI-REAGENT, Qiagen RNeasy mini-columns, MASTERPURE Complete DNA and RNA Purification Kit (EPICENTRE®, Madison, Wis.), Paraffin Block RNA Isolation Kit (Ambion, Inc.) and RNA Stat-60 (Tel-Test), the MassARRAY-based method (Sequenom, Inc., San Diego, Calif.), differential display, amplified fragment length polymorphism (iAFLP), and BeadArray™ technology (Illumina, San Diego, Calif.) using the commercially available Luminex100 LabMAP system and multiple color-coded microspheres (Luminex Corp., Austin, Tex.) and high coverage expression profiling (HiCEP) analysis.

The diagnostic methods described herein can employ contacting a patient's sample with a diagnostic reagent, as described above, which forms a complex or association with the ET-1 in the patients' sample. Detection or measurement of the sample ET-1 may be obtained by use of a variety of apparatus or machines, such as computer-programmed instruments that can transform the detectable signals generated from the diagnostic reagents complexed with the ET-1 in the biological sample into numerical or graphical data useful in performing the diagnosis. Such instruments may be suitably programmed to permit the comparison of the measured ET-1 in the sample with the appropriate reference standard and generate a diagnostic report or graph.

Such diagnostic methods useful herein include the methods described in the following Examples.

B. Diagnostic Compositions and Reagents

In conjunction with the performance of the various diagnostic techniques described herein, another aspect of the invention is a variant of diagnostic reagents employing the ET-1 biomarker. One embodiment of a diagnostic reagent comprises at least one polynucleotide immobilized on a substrate. The polynucleotide is a genomic probe that hybridizes to ET-1 cDNA and or ET-1 mRNA. The reagent can contain additional biomarkers useful as a genetic signature of IC. In one embodiment the reagent enables detection of changes in expression in ET-1 from that of a reference expression profile. In another embodiment, differences between the expression of ET-1 and additional biomarkers in a subject from that of the signature profile can indicate a diagnosis of IC.

Still another diagnostic reagent or composition or kit for diagnosing the occurrence, stage or progression of IC in a mammalian subject includes one or more PCR primer-probe sets that amplifies a polynucleotide sequence of ET-1. Another such composition or kit contains a second PCR primer-probe set that amplifies a polynucleotide sequence of a "second" IC biomarker, such as any of those identified above. The diagnostic compositions of the invention can be presented in the format of a microfluidics card, a microarray, a chip or chamber that employs the PCR, RT-PCR or Q PCR techniques described above. In one aspect, such a format is a diagnostic assay using TAQMAN® Quantitative PCR low density arrays. When a biological sample from a selected subject is contacted with the primers and probes in the diagnostic composition, PCR amplification of genes in the gene expression profile from the subject permits detection of changes in expression in the splicing factor genes in the gene expression profile from that of a reference gene expression profile. Significant changes in the gene expression indicating an increase in the expression level of ET-1 from that of the reference gene expression profile can correlate with a diagnosis of IC.

The selection of the polynucleotide sequences, their length and labels used in the composition are routine determinations made by one of skill in the art in view of the teachings of which genes can form the gene expression profiles suitable for the diagnosis and prognosis of IC. For example, useful primer or probe sequences can be at least 8, at least 10, at least 15, at least 20, at least 30, at least 40 and over at least 50 nucleotides in length. For example, such probes and polynucleotides can be complementary to portions of the coding or non-coding strand of the nucleotide sequences encoding ET-1 (see GenBank sequences referenced above). The probes and primers can be at least 70%, at least 80%, at least 90%, at least 95%, up to 100% complementary to sequences encoding ET-1 or to regulatory sequences flanking the ET-1 coding sequences.

Such diagnostic reagents useful in the methods described herein include the reagents described in the following Examples.

Still another diagnostic reagent includes a composition or kit comprising at least one ligand that binds to an expression product of ET-1. In one embodiment the ligand is associated with a detectable marker. In another embodiment, the ET-1 is a protein and said ligand is an antibody or functional fragment thereof, such as a Fab fragment, a complementarity determining region "CDR", an scFV, among other known sequences. Such reagents are useful in immunohistochemistry diagnostic methods. Antibodies or antisera, preferably polyclonal antisera, and most preferably monoclonal antibodies, or other protein-binding ligands specific for each factor are used to detect expression. The antibodies can be detected by direct labeling of the antibodies themselves, for example, with radioactive labels, fluorescent labels, hapten labels such as, biotin, or an enzyme such as horseradish peroxidase or alkaline phosphatase. Alternatively, unlabeled primary antibody is used in conjunction with a labeled secondary antibody, comprising antisera, polyclonal antisera or a monoclonal antibody specific for the primary antibody. Protocols and kits for immunohistochemical analyses are well known in the art and are commercially available. In still another embodiment, ET-1 is a nucleic acid sequence and said ligand is an antisense sequence or polynucleotide as discussed above.

Such diagnostic reagents and kits containing them are useful for the measurement and detection of ET-1 in the methods described herein for diagnosis/prognosis of IC. In such composition, the antibodies or peptides or nucleic acid sequences may be immobilized on suitable substrates, e.g., bound to an avidin-coated solid support, plates, sticks, or beads. Of course, other binding agents known to those of skill in the diagnostic assay art may also be employed for the same purposes. Other reagents include conventional diagnostic labels or label systems for direct or indirect labeling of the antibodies, peptides or nucleic acid sequences, with e.g., radioactive compounds, radioisotopes, such as $^{32}$P, $^{125}$I, techicium; fluorescent or chemiluminescent compounds, such as FITC, rhodamine or luciferin; and proteins such as biotin or enzymes and enzyme co-factors, such as alkaline phosphatase, β-galactosidase or horseradish peroxidase; and/or molecular labels such as FLAG, etc. Other elements of the label systems include substrates useful for generating the signals upon interaction with the other components of the label system, e.g., a streptavidin and horseradish peroxidase system. Any method known in the art for separately conjugating the antibody to the detectable moiety may be employed, including those methods described by Hunter et al, 1962 Nature 133:945; Pain et al 1981 J. Immunol., Meth. 40:219 and other conventional texts.

Alternatively, a diagnostic kit thus also contains miscellaneous reagents and apparatus for reading labels, e.g., certain substrates that interact with an enzymatic label to produce a color signal, etc., apparatus for taking blood samples, as well as appropriate vials and other diagnostic assay components.

C. Therapeutic Methods and Reagents

In still another aspect, methods for treating interstitial cystitis are provided. A method for treating interstitial cystitis involves delivering to a mammalian subject in need thereof a therapeutic composition that inhibits the action, production or synthesis of ET-1 in urine or urothelial cells of the subject. In another aspect, the method involves delivering to a mammalian subject in need thereof a therapeutic composition that inhibits the binding of ET-1 with its receptors on urothelial cells of the subject. In another aspect, the method involves delivering to a mammalian subject in need thereof a therapeutic composition that inhibits the expression of ET-1 in the urothelial cells of the subject.

The expression of ET-1 and its action may be inhibited by antagonists to ET-1, antagonists to ET-1 receptors ($ET_A$ and $ET_B$) and/or inhibition of its expression by the urothelial cells by RNA interference technology. The phrase "ET-1 antagonist" means an agent that inhibits the synthesis of ET-1 by the urothelial cells or an agent that binds ET-1 and forms a complex, which complex cannot bind to ET-1 receptors. The phrase "ET-1 receptor antagonist" means an agent that binds $ET_A$ and/or $ET_B$, thereby preventing binding between ET-1 and its receptors. Such antagonists may include, e.g., polynucleotides, siRNA fragments thereof, antibodies, fragments thereof and or small chemical molecules. In another aspect of the method, the composition is an ET-1 antagonist or ET-1 receptor antagonist that blocks the binding between ET-1 and its receptors. In one embodiment the composition down-regulates ET-1 expression by urothelial cells. In another embodiment, the down-regulation is mediated by siRNA. In still another embodiment, the antagonist is an antibody or fragment thereof that binds ET-1 or an ET-1 receptor antibody or fragment thereof (anti-$ET_A$ antibody or anti-$ET_B$ antibody). The choice of antagonist, e.g., whether protein antagonist, such as an antibody or antibody fragment that binds ET-1, or a nucleic acid inhibitor, such as an anti-sense sequence, siRNA, or a small molecule antagonist that inhibits the ET-1 or $ET_A$ or $ET_B$ receptors, may be selected by one of skill in the art.

In another therapeutic aspect, ET-1 has been shown to inhibit the proliferation of epithelial cells. Inhibition of urothelial proliferation by ET-1 requires the binding of ET-1 to its receptors ($ET_A$ & $ET_B$) on the urothelial cells. Therefore, ET-1, produced by the urothelial cells or produced elsewhere and excreted in the urine collected in the bladder cavity itself serves as an undesirable anti-proliferative agent. ET-1 prevents the repair and regeneration of urothelial cells and minimizes the urothelial barrier in certain conditions. Maintenance of the barrier is important for preventing the urinary solutes from diffusing into the bladder wall, and causing inflammatory changes and irritation common in IC.

Thus, in one embodiment, a therapeutic method involves inhibiting the production or synthesis of ET-1, and/or ET-1 receptors, to decrease the action of ET-1, particularly in the bladder. This is accomplished by delivering to the target cell an effective amount of an antagonist of ET-1 or an antagonist of the ET-1 receptors that prevents binding between ET-1 and its receptors. In one embodiment, the delivery comprises administering a plasmid or viral vector comprising a polynucleotide encoding an antagonist of ET-1 or an antagonist of the ET-1 receptors, or a functional fragment thereof under the control of a promoter operable in eukaryotic epithelial cells. In another embodiment, the delivery comprises administering an ET-1 antagonist or ET-1 receptor antagonist as a protein ectopically to the cell. In still a further embodiment, delivery occurs under conditions permitting the uptake of ET-1 antagonist or ET-1 receptor antagonist by the cell. In another embodiment, the ET-1 antagonist or ET-1 receptor antagonist is administered in an amount sufficient to prevent damage to the bladder wall. In another embodiment, the ET-1 antagonist or ET-1 receptor antagonist is administered in an amount to treat IC.

Thus, in one embodiment a therapeutic composition includes a plasmid or viral vector comprising a polynucleotide encoding ET-1 antagonist or an ET-1 receptor antagonist thereof under the control of a promoter operable in eukaryotic epithelial cells in a pharmaceutically acceptable vehicle or carrier. The selection of a suitable plasmid backbone or viral vector, of which many are well known in the art and commercially available may be done by a person of skill in the art. Examples of such vectors include recombinant adenoviral vectors, herpes simplex virus (HSV)-based vectors, adeno-associated viral (AAV) vectors, hybrid adenoviral/AAV vectors, recombinant retroviruses or lentiviruses which are constructed to carry or express a selected nucleic acid composition of interest, modified vaccinia virus Ankara (MVA), Vaccinia, Adeno-associated virus (AAV), Alphavirus etc. Retrovirus vectors that can be employed include those described in EP 0 415 731; International Patent Publication Nos. WO 90/07936; WO 94/03622; WO 93/25698; and WO 93/25234; U.S. Pat. No. 5,219,740; International Patent Publication Nos. WO 93/11230 and WO 93/10218; GB Patent No. 2,200,651; and EP 0 345 242, among others. Alphavirus-based vectors may also be used as the nucleic acid molecule encoding the transgene. Such vectors can be constructed from a wide variety of alphaviruses, including, for example, Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532). Representative examples of such vector systems include those described in U.S. Pat. Nos. 5,091,309; 5,217,879; and 5,185,440; and International Patent Publication Nos. WO 92/10578; WO 94/21792; WO 95/27069; WO 95/27044; and WO 95/07994. Such selection of vector and expression system is not believed to limit this invention.

In another embodiment, a therapeutic composition for administration to a human subject for treatment of a disease related to expression of ET-1 includes siRNA, that downregulates the production of ET-1 by urothelial cells, under the control of a promoter operable in eukaryotic epithelial cells in a pharmaceutically acceptable vehicle or carrier. In another embodiment, a therapeutic composition for administration to a human subject for treatment of a disease related to expression of ET-1 includes an ET-1 antagonist under the control of a promoter operable in eukaryotic epithelial cells in a pharmaceutically acceptable vehicle or carrier.

In still another embodiment, a pharmaceutical composition for administration to a human subject for treatment of a disease related to IC or expression of ET-1 contains an effective amount of an antagonist of ET-1 or an $ET_A$ or $ET_B$ antagonist in protein form in a pharmaceutically acceptable vehicle. This composition may be infused intravesically to the bladder cavity to minimize the cardiovascular effect of ET-1 antagonists.

As defined herein, pharmaceutically acceptable vehicles or carriers suitable for use in these compositions are well known to those of skill in the art and may be readily selected by same. In one embodiment, a preferred pharmaceutical carrier contains water for injection with mannitol added for tonicity at a concentration of about 45 mg/mL. Other possible carriers include, without limitation, and depending upon pH adjustments, buffered water, buffered saline, such as 0.8% saline, phosphate buffer, 0.3% glycine, hyaluronic acid, alcoholic/aqueous solutions, emulsions or suspensions. Other conventionally employed diluents, adjuvants and excipients, may be added in accordance with conventional techniques. Preservatives and other additives such as, for example, antimicrobials, antioxidants, chelating agents, inert gases and the like may also be provided in the pharmaceutical carriers. The preparation of these pharmaceutically acceptable compositions, from the above-described components, having appropriate pH isotonicity, stability and other conventional characteristics is within the skill of the art. See, e.g., texts such as Remington: The Science and Practice of Pharmacy, 21st ed, Lippincott Williams & Wilkins, publ., 2005; and The Handbook of Pharmaceutical Excipients, $6^{th}$ edit., eds. R. C. Rowe et al, APhA Publications, 2009.

As used herein, the term "effective amount" or "pharmaceutically effective amount" refers to the amount of active compound or pharmaceutical agent that elicits the biological or medicinal response in a tissue, system, animal, individual or human that is being sought by a researcher, veterinarian, medical doctor or other clinician, which includes one or more of the following: (1) preventing the disease; e.g., preventing a disease, condition or disorder in an individual that may be predisposed to the disease, condition or disorder but does not yet experience or display the pathology or symptomology of the disease; (2) inhibiting the disease; e.g., inhibiting a disease, condition or disorder in an individual that is experiencing or displaying the pathology or symptomology of the disease, condition or disorder (i.e., arresting or slowing further development of the pathology and/or symptomology); and (3) ameliorating the disease; e.g., ameliorating a disease, condition or disorder in an individual that is experiencing or displaying the pathology or symptomology of the disease, condition or disorder (i.e., reversing the pathology and/or symptomology). For example, an effective amount, when administered to a subject to treat IC, is an amount of a therapeutic sufficient to inhibit, slow, reduce, or eliminate inflammation, bladder pain and sensitivity and reduce ET-1 levels to a normal range. For example, an effective amount of an ET-1 receptor antagonist or ET-1 antagonist as a therapeutic is an amount sufficient to increase proliferation of urothelial cells in the bladder.

The amounts of ET-1 antagonists or ET-1 receptor antagonists in the pharmaceutical formulations can vary widely, i.e., from less than about 0.1 mg/mL, usually at or at least about 2 mg/mL to as much as 20 mg/mL, or alternatively up to 50 mg/mL or more by weight, and will be selected primarily by fluid volumes, viscosities, etc., in accordance with the particular mode of administration selected. Dosages will also be adjusted for the severity of disease, type of disease, and physical condition of the subject as determined by a physician.

A human unit dose form is typically included in a pharmaceutical composition that comprises a human unit dose of an acceptable carrier, preferably an aqueous carrier, and is administered in a volume of fluid that is known by those of skill in the art to be used for administration of such compositions to humans (see, e.g., Remington's Pharmaceutical Sciences, 17th Edition, A. Gennaro, Editor, Mack Publishing Co., Easton, Pa., 1985).

Similarly as therapeutic compositions, the mode of administration for in vivo administration may be selected by one of skill in the art, and can include any suitable route. Such routes may be selected from, e.g., oral, intravenous (i.v.), infusion, parenteral (aside from i.v., such as intralesional, intraperitoneal and subcutaneous injections), intraperitoneal, transdermal (including all administration across the surface of the body and the inner linings of bodily passages including epithelial and mucosal tissues). Other routes of administration are also feasible and include, without limitation, liposome-mediated delivery or implant delivery.

D. Screening Assays for the Identification of Useful Compounds

As disclosed herein, Endothelin-1 is a potential target for development of a therapeutic to treat interstitial cystitis. Antagonists to ET-1 or to its receptors are potentially useful as a therapeutic to prevent binding between ET-1 and its receptors and reduce symptoms associated with IC and enable the cells in the urothelial lining to repair themselves.

In another aspect, a method for screening a test compound or molecule for use in treating IC includes contacting a test compound with a mammalian urothelial cell expressing ET-1 or the receptors $ET_A$ and/or $ET_B$; and measuring the effect of the test compound on the expression level of ET-1 or its receptors. A decrease in the normal expression of ET-1 by the cell indicates a compound or molecule useful in therapy of IC. Thus, ET-1 and/or its receptors may also be used in the screening and development of chemical compounds, small molecules, nucleic acid sequences, such as cDNAs, or proteins which affect the expression of ET-1, and thus have utility as therapeutic drugs for the treatment of IC. In one embodiment, a test compound, including small molecules, peptides or polypeptides, nucleotide sequences, such as cDNAs or miRNAs, are selected for testing. The selected test compound is contacted or exposed to a mammalian cell expressing ET-1 or its receptors. After suitable culture conditions, e.g., 37° C. for about 48-60 hours, the effect of the compound on the expression level of the gene product is assessed by any suitable means. The effect of the compound to alter the normal expression of ET-1 is related to its impact on the expression level of the gene product or receptors by said cell. Where the effect is that the compound allows maintenance of normal expression levels or decreases elevated levels of ET-1, allowing normal expression of ET-1, that test compound is indicated to be useful as a potential therapeutic compound in the treatment of IC. Where the effect is that the compound increases the expression level of ET-1, the compound is indicated to have a potential adverse effect on inflammatory conditions of the bladder, such as IC.

A high throughput splicing assay used to identify compounds that change expression of ET-1 by urothelial cells may also be used to screen compounds. In one embodiment such an assay involves contacting in each individual well of a multi-well plate a different selected test compound (e.g., nucleotide sequence, amino acid sequence, small molecules, etc) with a mammalian urothelial cell that expresses a normal level of ET-1 or ET-1 receptors. In one embodiment that cell is transfected with a minigene that expresses luciferase (or another marker gene) only when said cell expresses ET-1 at a certain level. After the compound has been exposed to the expressing cell under appropriate culture conditions, the level of the marker gene (or luminescence) is conventionally measured. A change in the expression of the ET-1 level normally expressed by the cell caused by any of the test compounds is correlated with the expression or lack of expression of the marker in each well. For example, where such an assay is utilized to screen test compounds, the maintenance or a decrease in expression level of ET-1 is indicative that the compound has a potential therapeutic effect. A result in which there is an increase in expression level of ET-1 is indicative that the compound has a potential inflammatory or adverse effect on IC.

Other conventional assays and techniques also exist for the identification and development of compounds and drugs which impact the expression or activity of ET-1, such as methods described in publications referenced herein. Such other assay formats may be used and the assay formats are not a limitation.

E. Examples

The examples that follow do not limit the scope of the embodiments described herein. Our preliminary studies on bladder from IC patients showed upregulation of ET-1 in the bladder epithelium and submucosal mesenchymal cells when compared to that of normal. Urothelial cells cultured from IC patients also revealed an overexpression of ET-1 compared to those cells cultured from normal individuals. One skilled in the art will appreciate that modifications can be made in the following examples which are intended to be encompassed by the spirit and scope of the invention.

Example 1

General Experimental Methods

A. Statistics

Data are described appropriately before proceeding to analysis. Biomarker expression and all other continuous data are presented as sample means (±SEM). Graphical methods are used to examine the distribution and quality of the data. Group comparisons are performed using ANOVA. Categorical variables are summarized by proportions and compared across groups using standard chi-square tests of association. Exact p-values from Fisher's exact test are calculated for these tests. Logistic regression models are used to identify which patient demographics, study sites, and other clinical factors are predictive of particular phenotypes. In addition, statistical tests for univariate associations between clinical phenotypes and biomarkers are computed using Statistical analysis software (SAS; SAS, Cary, N.C.). Adjustments for clinical sites are made for most analyses. Separate multivariable predictive models are developed for each clinical phenotype incorporating the statistically significant biomarkers identified in the univariate analyses. After adjusting for statistically significant clinical variables, such as age, menopausal status, gender, and BMI, the selected biomarkers are entered sequentially in a forward selection model, with adjustments for cluster effects among subjects within clinical centers.

Unless mentioned otherwise, data are expressed as mean±standard error. Sample size calculation are based on preliminary data suggesting a difference between normal control and IC patients (or vulvodynia, or prostatitis) with a=0.05 and power=0.8. Data from western, Real-time PCR and Northern are quantified and statistically analyzed. Observations from these three groups are compared using a one-way ANOVA (analysis of variance), followed by Bonferroni corrections for multiple comparison procedures. Differences are considered significant at $P<0.05$. (JMP® 7, SAS, Cary, N.C.).

B. Fixation and Embedding:

Bladder tissues are fixed in 4% paraformaldehyde in PBS (pH 7.4) at 4° C. for 2 hours. Tissues are washed three times in PBS for 30 minutes each, dehydrated in an ascending ethanol series (30, 50, 70, 85, 95 and 100%), infiltrated into Technovit 7100 (Hereaus Kulzer GmbH & Co. KG, Wehrheim, Germany) overnight, and embedded in Technovit 7100 at room temperature by adding the polymerization agent provided in the kit.

C. Sectioning and Immunostaining:

Semithin sections (2-3 μm) are prepared using a LKB rotary retracting microtome with a tungsten carbide blade. For histological study, slides are stained with hematoxylin and eosin. Deparaffinized sections are washed in phosphate buffered saline (PBS) and blocked with 1% BSA for 1 hour. Then, the sections are incubated with the primary antibody at 4° C. Slides are washed three times for 5 minutes each in PBS and incubated with Texas Red–conjugated antimouse IgG (Sigma) diluted at 1:250 for 2 to 4 hours at room temperature, washed three times in PBS and mounted in Aqua-Poly/Mount medium. Sections are examined with a fluorescence microscope (Nikon E800) equipped for confocal microscopy.

D. RNA Extraction and Real Time PCR:

Total RNA are isolated from frozen tissue using Trizol reagent (Invitrogen, Carlsbad, Calif.) according to the manufacturer's protocol. RNA concentrations are measured by UV spectrophotometer. 1.0 μg of total RNA are reverse transcribed with oligo (dT) primer (Promega, Madison, Wis.) and M-MLV reverse transcriptase (GIBCO, Gaithersburg, Md.) at 37° C. for 1 hour. Then the cDNA are heated to 90° C. for 5 to inactivate the reverse transcriptase. 1 μL of this reverse transcription reaction are subjected to real time PCR amplification in the ABI 7500 Fast System (Applied Biosystems, Calif.). The following reaction components are prepared: 1 μL TaqMan Assay (20×), 1 μL RT, 8 μL water and 10 μL universal mix (Applied Biosystems). GADPH and p-actin are used as internal control for target genes expression.

E. Protein Expression and Western Blotting:

Total extractable protein are isolated from frozen tissues in 1% SDS extraction buffer (100 mg tissue/ml) containing 20% glycerol, 50 mM Tris-HCl (pH 6.8), 0.5% (v/v) Tween-20 and protease inhibitors (0.5 mM PMSF, 2 μM pepstatin, 2 μM antipain and 0.1 mg/ml trypsin inhibitor). Protein concentration in the supernatant are measured using the Bio-Rad DC protein assay kit. 20 μg of total extract protein are loaded on SDS-PAGE gels. Then the protein are transferred to Immobilon-P membrane with transfer buffer [25 mM Tris, 96 mM glycine plus 50 mg SDS and 0.5 ml-mercaptoethanol in 1 liter buffer] for myosin and transfer buffer [25 mM Tris, 192 mM glycine and 20% (v/v) methanol] for other small proteins overnight at 4° C. Then membranes are blocked in 5% non-fat milk for 1 hour and incubated with primary antibody for 2 hour at room temperature. Then the membranes are washed with TBST buffer (20 mM Tris, 500 mM NaCl, 0.05% Tween 20) 3 times and incubated with second antibody for 1 hour. After three additional TBST buffer washes, substrates in the membrane can be visualized by using ECL kit (Amersham Pharmacia Biotech). Band intensities are scanned and analyzed using Fujifilm 1AS-3000 imager and MultiGauge v3.0 Software program (Fuji Photo Film, Japan). Standard curves for all proteins analyzed are constructed to establish the linear concentration ranges.

F. Immunostaining:

Cross-sections (5 micron) of tissue sections are made from the paraffin blocks. Tissue sections are deparaffinized and put into descending grades of alcohol and then blocked 30 minutes in 1% BSA solution. After blocking, sections are incubated for 2 hours at room temperature with the primary antibodies specific for target proteins. After washing 3 times in PBST, the sections are then treated with second antibody according to primary antibody, then washed again 3 times with PBST. Finally slides are mounted with a drop of mounting medium (Aqua-Mount, Lerner Labs; Pittsburgh, Pa.) and viewed under a Nikon (Melville, N.Y.) Eclipse 800 fluorescence microscope. Images are captured using a RT Slider SPOT camera (Diagnostic Instruments; Sterling Heights, Mich.) and Image-Pro Plus software from Media Cybernetics (Silver Spring, Md.). A negative control, in which only the secondary antibody is added, is used for all samples.

G. In Situ Hybridization:

Tissue are fixed in 4% paraformaldehyde in 0.1 M phosphate buffer (PB) (pH 7.4) (4% PFA) at 4° C. overnight. After fixation, tissue is embedded into paraffin. Cross-sections are cut at 5 μm. Probes of sense and antisense digoxigenin (DIG)-labeled RNA strands are transcribed in vitro from target sequences using an RNA labeling kit (Boehringer). In situ hybridization is performed as follows: Sections are deparaffinized, hydrated and treated with proteinase K (Boehringer, 10 mg/ml) and then hybridized using sense or antisense DIG-labeled RNA probe at 60° C. for 18-24 h. Hybridization signals are then detected by using alkaline phosphatase-conjugated anti-DIG antibody (Boehringer) and NBT as the chromogen. Each in situ hybridizations are performed in duplicate and slides are visualized and photographed using a Nikon Eclipse E800 microscope and Spot digital camera.

Example 2

The Expression of ET-1 in the Urinary Bladder Epithelium

The expression of ET-1 in the urothelium in the bladder biopsies from IC patients is analyzed at the mRNA and protein level by RT-PCR (and Real-time PCR) and Western blot analysis, respectively. The relative increase in the expression of the endothelin at the mRNA level is assessed by quantitative real-time PCR using the published procedure[37]. Immunofluorescence microscopy is used for in situ localization of the endothelin expression to the urothelial cell layer. For immunofluorescence microscopy, formalin-fixed tissue sections of bladder biopsies previously obtained for the 1CDB (Interstitial Cystitis Database) were prepared as described above. The detailed procedure for performing the immunofluorescence microscopy is provided in Example 1. Briefly, Anti-ET-1 antibody (Calbiochem, San Diego, Calif.; cat. #CP44) is used at a dilution of 1:400 and anti-mouse IgG-Cy3 secondary antibody (Sigma, St. Louis, Mo.; C-2181) at a dilution of 1:200. The cellular localization of ET-1 in the bladders from both control and IC patients is determined. Sections are double immunostained using antibody to actin conjugated to FITC, followed by antibody against ET-1, to aid in determining whether the submucosal smooth muscle cells also express ET-1 and if this expression is increased in IC.

Results from the immunofluorescence microscopic analyses provide information concerning the in situ localization of the ET-1 in the tissue (e.g., whether there is more in the urothelium compared to the smooth muscle layer). One photomicrograph of a histological section (5 micron in thickness) was taken from the bladder of a woman with interstitial cystitis who died of other causes (figure not shown) Immunofluorescence microscopy was used for in situ localization of the endothelin expression in the urothelial cell layer using a commercially available antibody against ET-1 as discussed in Example 1. At several areas, the urothelium was denuded although it was preserved in some areas. This preliminary experiment revealed the presence of ET-1 in the urothelium and the submucosal mesenchymal. The collagenous connective tissue and red blood cells in the capillaries in section from IC showed autofluorescence. This tissue section from the IC patient showed intense immunofluorescence compared to a section taken from the normal region of the bladder cystectomy for a healthy patient, using the procedures of Example 1 below (figure not shown), and also revealed hyperemia and hemorrhage. The preliminary results of these analyses demonstrate that Endothelin-1 (ET-1) is highly expressed in the urothelium of patients with interstitial cystitis (IC) compared to normal patient bladder urothelium.

In another experiment, human urothelial cells from a biopsy of a normal woman from which cells have been sub-cultured and sub-cloned several times to obtain a homogeneous population of epithelial cells. These cells have become a stable cell line that maintains the epithelioid phenotype and expresses uroplakin. Karyotype analysis revealed that the cells are tetraploid but maintain stable chromosome numbers (79 chromosomes) and urothelial phenotype. These cells express uroplakin protein when stained with Uroplakin II stain and DAPI, which stains nucleii (figure not shown) and confirms the normal urothelial cell phenotype. The cultured urothelial cells also express both Endothelin-1 receptor A and Endothelin-1 receptor B with appropriate staining (figures not shown).

In still another experiment, rabbit and human urothelial cells were cultured. Human urothelium cell culture was performed and it was observed that the cells maintain normal morphology after multiple passages. Sufficient number of rabbit urothelial cells were obtained from primary cultures. These cells can be used as primary culture or as one passage for the proliferation assay. Under 100× magnification (photograph not shown) the rabbit urothelial cells after one passage show epithelioid morphology and express uroplakin II and endothelin receptors. Similarly under 200× magnification (photograph not shown) human urothelial cells after 20 passages show epithelioid morphology ad express uroplakin II and endothelin receptors.

In another experiment, human urothelium cells from a biopsy of a normal woman have been sub-cultured and sub-cloned several times until the cell culture has now become a stable cell line with tetraploid chromosomes. These cells express uroplakin protein using Uroplakin II staining and DAPI, which stains nuclei (photograph not shown). These observations confirm normal urothelial cell phenotype. In addition, cultured urothelial cells express both Endothelin-1 receptor A and Endothelin-1 receptor B (photographs not shown).

Example 3

Expression of ET-1 in the Urine of Patients with IC

Endothelin expression is quantitated at the protein level by enzyme linked immunosorbent assay (ELISA). ELISA is performed using the human big Endothelin-1 (ET-1) Enzyme Immunometric Assay kit (Assay Designs, Inc., Ann Arbor, Mich.) to determine human big ET-1 peptide levels in urine samples from five female IC patients. The normal control group was urine samples from four normal healthy females. The ET-1 primary antibody shows little to no cross-reactivity with related endothelin peptides including ET-2 and ET-3. The immunoassay kit has a sensitivity as low as 0.14 pg/ml. Because the two-site "Sandwich" ELISA assays require two antibodies, they can be more specific than RIA assays[40].

Briefly the appropriate number of wells in a 96 well microtiter plate coated with rabbit antibody specific to human ET-1 are washed twice with wash buffer containing phosphate buffered saline with detergent. Next 100 μL of either standard, clarified urine, or plasma is added, the plate mixed, sealed and incubated at 37° C. for 1 hour. Then the wells are washed for a total of 7 times with wash buffer and inverted and tapped on a paper towel. Next 100 μL of rabbit antibody to human IgG conjugated with horseradish peroxidase is added and incubated at 37° C. for 30 minutes at room temperature in the dark. The reaction is stopped with a solution of 1N sulfuric acid in water. The plate is read in a microplate reader at 450 nm with correction at 590 nm.

The level of ET-1 in normal human urine is estimated to be in the range of 1.0 to 4.0 pg/ml, which falls easily in the linear range of this assay. The data from this analysis shows that urine of patients with IC demonstrates an elevation of ET-1 (FIG. 1). The average ET-1 level is 2.9±1.9 pg/ml in urine from the normal control group, while the average ET-1 level increased to 10.7±2.3 pg/ml in urine from the five IC patients. These data indicate that there is a greater than three-fold increase of Endothelin-1 in the urine of patients with IC than in the urine of healthy women. These data demonstrate a correlation between elevations of urinary ET-1 and IC that has not been shown before; thus a determination of urinary ET-1 serves as a biomarker for the diagnosis of IC.

An increase in ET-1 levels in urine or an increased level of ET-1 in the bladder tissue suggests an upregulation of the endothelin signal transduction pathway in the urothelium associated with IC. An increase in the level of ET-1 in either the urothelial extract or in the urine of IC patients compared to normal controls suggests that the mature ET-1 is being synthesized at a higher rate in the IC patients. Without being bound by theory, the mechanistic basis of this increase could be due to an upregulation of endothelin converting enzyme (ECE) which converts the ET-1 precursor known as Big ET-1 to the mature 21 amino acid ET-1 peptide, etc.

Example 4

Effect of ET-1 on the Proliferation of the Urothelial Cells

The overexpression of ET-1 in urothelial cells cultured from IC patients (Example 2) may have an inhibitory effect on the proliferation of urothelial cells, similar to that on epithelial proliferation in the lung. Upregulation of ET-1 in cells in the submucosa would lead to proliferation of these cells associated with remodeling of the bladder wall. On the other hand, upregulation of the ET-1 in the urothelial cells would lead to inhibition of urothelial proliferation if the ET-Fs effect on the urothelium is similar to respiratory epithelium. Thus, it is important to determine whether ET-1 also plays a role in the turnover of urothelial cells, at least in some subsets of IC patients.

Experiment A:

The epithelial cell culture and proliferation assay used for these experiments is described. Briefly, explanted epithelial cells propagated from fresh biopsy specimens are grown in DMEM-F12 with 10% heat-inactivated fetal bovine serum, 1% antibiotic/antimycotic, 1% L-glutamine, 1.0 unit/ml insulin (all from Sigma), and 5 µg/ml human epidermal growth factor at 37° C. in a humidified atmosphere of 5% $CO_2$ and 95% air. Cultured cells are characterized to possess urothelial phenotype by binding AE-1/$AE_3$ pancytokeratin antibodies (Signet Laboratories, Dedham, Mass.). Cell proliferation is assessed also by $^3$H-thymidine incorporation and by cell counting using a haemocytometer. ET-1 samples are diluted at varying concentrations in serum-free MEM (containing only glutamine and antibiotics) and applied to cells. Control cultures receive only the vehicle. Cells are fed with serum-free medium for the proliferation assay.

Cultures are exposed to 1 µCi per well $^3$H-thymidine (1 Ci=37 GiBg) for 4 hrs and trypsinized, sedimented by brief centrifugation (3,000 rpm for 10 min) and the cell pellets are washed with a buffer containing cold thymidine and the radioactivity determined using a scintillation counter. The $^3$H-thymidine incorporation is expressed as a mean decrease in cpm of >2 SD from the mean of control cells for each plate. In addition, the $^3$H-thymidine treated cell cultures are fixed in 5% buffered formalin. Cultures are washed with ascending grades of ethanol (70%, 95% and 100%) and air dried. Dry cultures are coated with NTB2 autoradiographic emulsion (KODAK) in the dark room, air dried, stored in a dark box and exposed at 4° C. for 2 weeks. After developing the autoradiographs in D-19 (15° C.) and fixation, culture plates are stained with H &E. Cultures are examined under a light microscope and the number of cells showing silver grains in the nuclei from 10 selected fields on the culture plate are counted. The data are expressed as % of cell incorporating $^3$H-thymidine.

A concentration response curve is prepared using varying concentrations of ET-1. Decreased $^3$H-thymidine incorporation is plotted as a function of the ET-1 concentrations. Determining the cellular proliferation by autoradiography confirms the increased thymidine incorporation determined from the total radioactivity in the cell pellets.

Decreased $^3$H-thymidine incorporation by the urothelial cells in the presence of ET-1 indicates an anti proliferative effect for ET-1. In order to determine whether this effect is specific for urothelial cells, cultures for fibroblasts and detrusor smooth muscle cells established in our laboratory from human bladder biopsies are used as controls.

ET-1 inhibits the proliferation of urothelial cell cultured from both human and rabbit bladder. When cultured rabbit primary urothelial cells are treated with ET-1 at 20 µM, a 30-40% inhibition of growth of the cells is demonstrated (FIG. 2A). When cultured human primary urothelial cells are treated with 20 µM ET-1, the cell growth is inhibited. However, this inhibition is reversed by treating the cells with 1 µM PD145065 (a global ET-1 receptor antagonist that inhibits both $ET_A$ and $ET_B$; see FIG. 2B). The fact that the ET-1 receptor antagonist abolishes the ET-1-induced anti-proliferative effect shows that ET-1's effect is receptor-mediated. These data confirm that ET-1 has an inhibitory effect on urothelial proliferation.

The results of this assay demonstrate that ET-1 overexpression inhibits proliferation of urothelial cells in IC. This indicates that agents that inhibit the expression, production or synthesis of ET-1 can be used therapeutically to repair bladder wall linings.

Experiment B:

Click-iT EdU assay (Invitrogen) was used to detect and quantify newly synthesized DNA. EdU is a nucleoside analog of thymidine and is incorporated in DNA during active DNA synthesis. In Click-iT assay, EdU can be detected by green fluorescent dye and nuclei can be detected by blue fluorescent dye. Using fluorescent microplate reader (Synergy2, BioTek) both green and blue fluorescent signal were detected and quantified as shown in the bar graph of FIG. 3). Phase image and merged EdU and nucleic staining images for both control and ET-1 treated urothelial cells (figures not shown) demonstrated that the ET-1 treatment (10 nM, which is equal to 25 ng/ml) induced a significant decrease of EdU staining in cultured urothelial cells, which means less newly synthesized DNA in the presence of ET-1.

An increase in the level of ET-1 in the urine of IC patients over levels in controls suggests that the mature ET-1 is synthesized at a higher rate in the IC patients. The increase may be due to up-regulation of endothelin converting enzyme (ECE), which converts the ET-1 precursor known as Big ET-1 to the mature 21 amino acid ET-1 peptide. The results from the immunofluorescence microscopy analyses provide information concerning the in situ localization of the ET-1 in the tissue (e.g., greater expression in the epithelial compared to the smooth muscle layer or in different cells in the transitional epithelium, such as, basal cells versus intermediate or umbrella cells). An increase in ET-1 levels in urine or an increased level of ET-1 in the bladder tissue suggests up-regulation of the endothelin signal transduction pathway in the urothelium in IC. If ET-1A and ET-1B receptors are over-expressed in urothelial and sub-urothelial tissues from patients with symptoms associated with IC (when compared to control patients but not in tissues that do not contribute to a particular phenotype), then these biomarkers are specific for the IC clinical phenotype and/or of subtype of IC.

The ET-1 biomarker, found to correlate with disease presence, is a diagnostic tool and also a tool to follow disease progression, especially the changes in the integrity of the urothelium and subsequent pathologic insult to the suburothelial tissue including the nerve terminals. This biomarker provides insight into therapeutic targets for disease treatment. Specifically, the signaling mechanisms responsible for transcription of this biomarker suggests a means by which the disease progresses and by which prevention can be achieved. In one embodiment, if urinary ET-1 is increased in any of the non-IC lower urinary tract disorders, one may correlate the ET-1 urinary biomarker with clinical signs of IC, and also with the presence of one or more of the pro-inflammatory cytokines (such as IL1β, IL-6 or IL-8) which has been associated with IC.

Decreased 3H-thymidine incorporation by urothelial cells in the presence of ET-1 indicates an anti-proliferative effect of ET-1. To determine whether this effect is specific for urothelial cells, cultures for fibroblasts and detrusor smooth muscle cells established in our laboratory from human bladder biopsies are used as controls. Proliferation assays in the presence of ET-1 receptor antagonists demonstrate that the observed effect on proliferation is in fact mediated via ET-1 binding to its receptors.

All documents identified of listed herein, as well as the specification of provisional U.S. patent application No. 61/246,273, are incorporated herein by reference. While various embodiments in the specification or claims are presented using "comprising" language, under various circumstances, a related embodiment may also be described using "consisting of" or "consisting essentially of" language. It is to be noted that the term "a" or "an", refers to one or more, for example, "a reagent," is understood to represent one or more reagents. As such, the terms "a" (or "an"), "one or more," and "at least one" are used interchangeably herein. While the invention has been described with reference to specific embodiments, it is appreciated that modifications can be made without departing from the spirit of the invention. Such modifications are intended to fall within the scope of the appended claims.

PUBLICATIONS (1) Jones C A, Nyberg L., *Urology* 1997 May; 49(5A Suppl): 2-9.
(2) Tomaszewski J E, et al., *Urology* 2001 June; 57(6 Suppl 1):67-81.
(3) Pauwels E, et al., *J Urol* 2004 April; 171(4):1567-70.
(4) Steinkohl W B, Leach G E. *Urology* 1989 December; 34(6):399-401.
(5) Shea V K, et al, *J. Neurophysiol* 2000 October; 84(4): 1924-33.
(6) Su X, et al, *J Neurophysiol* 1997 March; 77(3): 1566-80.
(7) Parsons C L, *Urol Clin North Am* 1994 February; 21(1):93-100.
(8) Keay S K, et al. *Proc Natl Acad Sci USA* 2004 Aug. 10; 101(32):11803-8.
(9) Parsons C L, et al, *J Urol* 1998 June; 159(6): 1862-6.
(10) Dell J R. *Int J Fertif Womens Med* 2003 July; 48(4):154-62.
(11) Kim J, et al. *FEBS Lett* 2007 Aug. 7; 581(20):3795-9.
(12) Hanno P. Painful bladder syndromes. In: Hanno P M, Markowicz S B, Wein A J, editors. *Clinical Manual of Urology* New York: McGraw-Hill; 2001. p. 199-212.
(13) Ferreira S H, et al, *J Cardiovasc Pharmacol* 1989; 13 Suppl 5:S220-S222.
(14) Kaski J C, et al. *Br Heart J* 1995 December; 74(6):620-4.
(15) Raffa R B, et al, *Life Sci* 1991; 49(11):L61-L65.
(16) D'Amico M, et al. *Pain* 1996 May; 65(2-3):205-9.
(17) Piovezan A P, et al., *Eur J Pharmacol* 1998 Jun. 12; 351(1):15-22.
(18) Carducci M A, et al. *J Clin Oncol* 2002 Apr. 15; 20(8): 2171-80.
(19) Khodorova A, et al. *J Neurosci* 2002 Sep. 1; 22(17): 7788-96.
(20) Panettieri R A, Jr., et al., *Br J Pharmaco* 1996 May; 118(1): 191-7.
(21) Fisher S A, et al, *Circ Res* 1997 June; 80(6):885-93.
(22) Sumpio B E, et al, *Surgery* 1990 August; 108(2):277-81.
(23) Birder L A, et al, *Am J Physiol Renal Physiol* 2003 September; 285(3):F423-F429.
(24) Sun Y, et al, *J Urol* 2001 November; 166(5):1951-6.
(25) Ohta K, et al., *Biochem Biophys Res Commun* 1990 Jun. 15; 169(2):578-84.
(26) Lotz M, et al, *J Urol* 1994 September; 152(3):869-73.
(27) Keay S, et al, *J Urol* 1996 December; 156(6):2073-8.
(28) Uehata M, et al., *Nature* 1997 Oct. 30; 389(6654):990-4.
(29) Shirasawa Y, et al., *Am J Physiol Heart Circ Physiol* 2003 December; 285(6):H2573-77.
(30) McGregor E, et al., *Cardiovasc Res* 2002 January; 53(1): 219-26.
(31) Yanagisawa M, et al, *Nature* 1988 Mar. 31; 332(6163): 411-5.
(32) Battistini B, et al., *Peptides* 1993 March; 14(2):385-99.
(33) Dosanjh A, et al., *J Asthma* 2003 December:40(8):883-6.
(34) Erickson D., et al. *J Urology* 2008 May; 179(5):1850-6. Epub 2008 Mar. 18.
(35) Erickson D R, *Urology* 2001 June; 57(6 Suppl 1):15-21.
(36) Zamore P D, et al., *Science* 2005 Sep. 2; 309(5740): 1519-24.
(37) Zhang E Y, et al., *Am J Pathol* 2004 February; 164(2): 601-12.
(39) Keay S, et al., *Urology* 2001 June; 57(6 Suppl 1):104.
(40) Davenport A P, Kuc R E. *Methods Mol Biol* 2002; 206: 21-36.
(41) Gamper et al., *BMC Genomics,* 2009; 10:199

What is claimed is:

1. A method for diagnosing interstitial cystitis (IC) in a female human subject comprising:
   obtaining a urine sample from a female subject having clinical symptoms of bladder pain and increased urinary frequency or urgency;
   contacting the urine sample with an antibody or antibody fragment that binds, and is capable of measuring the expression or activity of, a biomarker Endothelin 1 (ET-1) in an enzyme-linked immunosorbent assay,
   measuring the level of expression or activity of ET-1 in the subject's urine sample relative to the level of expression or activity in a reference population that consists of healthy female mammalian subjects; and
   diagnosing IC when measurement shows a significant elevation between the ET-1 concentration in the sample and the ET-1 concentration in the reference population.

2. The method according to claim 1, wherein the urine is diluted.

3. The method according to claim 1, wherein the urine is concentrated.

4. The method according to claim 1, wherein the significant elevation of ET-1 in the subject's sample is three-fold above that of the reference population.

5. The method according to claim 1, wherein said subject is being treated for IC and wherein the method enables a determination of the efficacy of the treatment.

* * * * *

SEQUENCE LISTING

<160> NUMBER OF SEQ ID NOS: 1

<210> SEQ ID NO 1
<211> LENGTH: 21
<212> TYPE: PRT
<213> ORGANISM: Homo sapiens

<400> SEQUENCE: 1

Cys Ser Cys Ser Ser Leu Met Asp Lys Glu Cys Val Tyr Phe Cys His
1               5                   10                  15

```
Leu Asp Ile Ile Trp
            20
```